Figure 1:
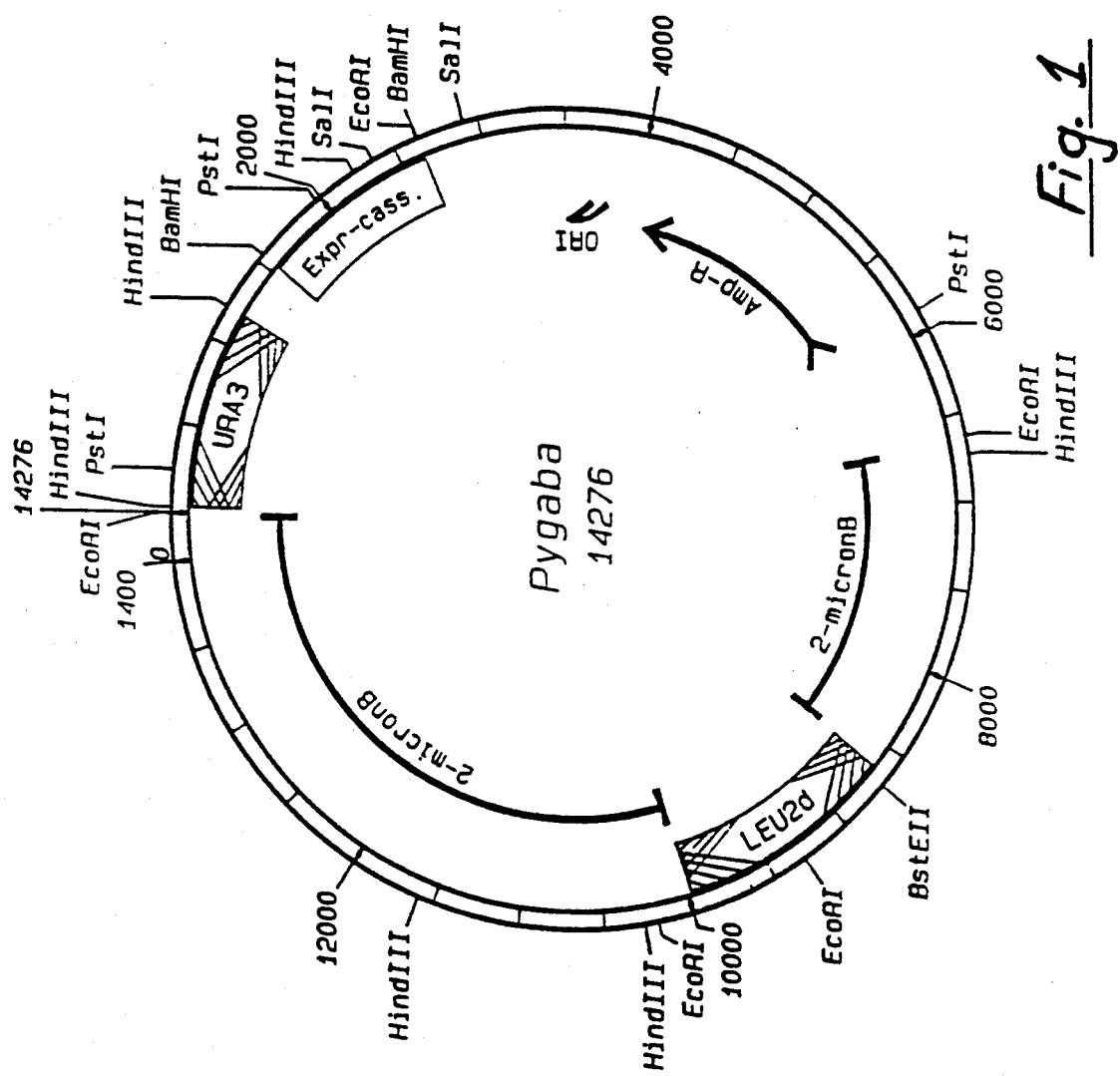

United States Patent [19]

Hansen et al.

[11] Patent Number: 5,149,777
[45] Date of Patent: Sep. 22, 1992

[54] HUMAN INSULIN ANALOGS AND PREPARATIONS CONTAINING THEM

[75] Inventors: Finn B. Hansen, Roskilde; Per Balschmidt, Espergaerde, both of Denmark

[73] Assignee: Novo Nordisk A/S, Bagsvaerd, Denmark

[21] Appl. No.: 640,308

[22] PCT Filed: Jul. 20, 1988

[86] PCT No.: PCT/DK88/00124

§ 371 Date: Mar. 19, 1991

§ 102(e) Date: Mar. 19, 1991

[87] PCT Pub. No.: WO90/01038

PCT Pub. Date: Feb. 8, 1990

[51] Int. Cl.$^5$ .................... A61K 37/26; A61K 37/02
[52] U.S. Cl. ................................................ 530/303
[58] Field of Search ............................ 514/3; 530/303

[56] References Cited

FOREIGN PATENT DOCUMENTS 0214826 3/1987 European Pat. Off. .
0254516 1/1988 European Pat. Off. .

OTHER PUBLICATIONS

Casaretto et al, Biol. Chem. Hoppe Seyler vol. 368 709–716 Jun., 1981.
Fischer et al, Biol. Chem. Hoppe Seyler vol. 366 521–515 May, 1985.
Peptides 1980, Proc. of the 16th European Peptide Symposium Helsingor, Denmark Aug. 31–Sep. 6, 1980 372–377.

Primary Examiner—Merrell C. Cashion, Jr.
Assistant Examiner—B. Celsa
Attorney, Agent, or Firm—Dann, Dorfman, Herrell and Skillman

[57] ABSTRACT

Novel human insulin analogs exhibiting high biological activity and in which the amino acid residue Phe$^{B25}$ is substituted by His or Tyr and moreover substitutions may optionally be present in one or more of the positions A4, A8, A17, A21, B9, B10, B12, B13, B21, B26, B27, B28, and B30, as well as the amino acid residue in the B30 position may further be totally missing or may be blocked at the C-terminal in the form of ester or amide.

20 Claims, 2 Drawing Sheets

HUMAN INSULIN ANALOGS AND PREPARATIONS CONTAINING THEM

TECHNICAL FIELD

The present invention relates to novel human insulin analogs exhibiting a high specific biological activity as well as insulin preparations containing the human insulin analogs of the invention.

BACKGROUND ART

Ever since the discovery of insulin in 1922 many different types of insulin preparations have been used for the treatment of Diabetes mellitus. At the beginning exclusively insulin solutions exhibiting a rapidly commencing and relatively rapidly ceasing insulin activity were used, but later on insulin preparations exhibiting a wider profile of activity procured by lowering of the solubility of insulin by means of additions as e.g. zinc salt and/or protamines have been produced. For reasons of availability the insulin used herefor has normally been recovered from Pancreas from domestic animals, most frequently oxes, pigs and sheep, however, recently preparations containing human insulin of biotechnological origin have also appeared on the market.

Throughout the years a large number of artificially prepared analogs of human insulin has been described, usually with the purpose of elucidating the influence of the structure on the activity, vide e.g. Märke et al., Hoppe-Seyler's Z. Physiol. Chem. 360, p. 1619-32 (1979). Investigations of the activity of substitutions of the (B22–B26)-sequence of the insulin on the receptor binding have been of particular interest, as said sequence is considered to be the main field of binding for the insulin receptor, and as naturally occurring mutations have been found with substitutions in said field. Vide e.g. S. Shoelson et al. PNAS 80, p. 7390-94 (1983) and M. Kobayashi et al.: Biomed. Res. 5 (3) p. 267-72 (1984). Very low activities for analogs in which Phe(B24) or Phe(B25) are replaced are thus found here, and therefore it is concluded that the presence of these two amino acids is of decisive importance to the receptor binding.

Replacements in the insulin molecule can also be introduced with the purpose of improving the profile of activity of the insulin in the treatment of Diabetes. Thus, e.g. Danish Patent Application No. 5457/86 discloses that one or more replacements of Glu in the insulin molecule by a neutral amino acid residue causes a shifting of the zone of precipitation of the insulin in such a way that a slow release after injection is obtained.

Moreover, Danish Patent Application No. 4116/86 discloses insulin analogs being particularly rapidly absorbed after injection. This effect is a result of the fact that by means of hydrophilic replacements in particular in the B9 and in the B28-positions in the insulin molecule a suppression of the aggregation ability of the insulin is obtained so that it is essentially present as monomer. However, a number of these insulin analogs exhibits a reduced biological activity.

Peptides 1980, Proceedings of the Sixteenth European Peptide Symposium Helsingor, Denmark, Aug. 31-Sep. 6, 1980, p. 372-377 describes the preparation of $[Tyr^{B25}, Ala^{B30}]$-human insulin by enzymatic coupling of the corresponding protected octapeptide to des-octapeptide (B23-B30) insulin followed by deprotection with trifluoroacetic acid. No data of biological activity is stated.

Biol. Chem. Hoppe-Seyler 1987, 368(6), p. 709-716 describes the preparation of analogs of des-(B26–B30)-insulin-B25-amide in which $Phe^{B25}$ is replaced by $Tyr^{B25}$ or $His^{B25}$ thereby obtaining an increased activity of 230 and 370%, respectively. The analogs are truncated and at the B25 position.

DISCLOSURES OF THE INVENTION

It has now surprisingly been found that certain human insulin analogs in which Phe in position B25 is replaced by His or Tyr and optionally further one or more of the amino acid residues in positions A4, A8, A17, A21, B9, B10, B12, B13, B21, B26, B27, B28, and B30 is replaced by another amino acid residue, and in which the amino acid residue in position B30 moreover may be missing totally or be blocked at the C-terminal in the form of ester or amide, exhibit a higher biological activity than in such case where Phe in position B25 is unchanged.

Accordingly, the present invention relates to human insulin analogs in which the amino acid residue in position B25 is His or Tyr, the amino acid residue in one or more of the positions A4, A8, A17, A21, B9, B10, B12, B13, B21, B26, B27, B28, and B30 is optionally replaced by another amino acid residue, and the amino acid residue in the B30-position is optionally missing or blocked at the C-terminal in the form of ester or amide, provided that when B25 is Tyr then B30 is different from Ala.

Examples of particularly preferred substitutions in the above indicated positions are: A4:Gln, A8:His, A17:Gln, A21:Asp, B9:Asp, B10:Asp, B12:Ile, B13:Gln or Arg, B21:Gln or Ile, B26:Glu, B27:Arg, B28:Asp, and B30:Ala or Ser, provided that when B25 is Tyr then B30 is different from Ala. If several substitutions are desired at the same time in the positions indicated above, it is preferred for reasons of use that they are present within the group: A4, A8, A17, B13, B21, B27, and B30, or within the group: A8, A21, B9, B10, B12, B26, B28, and B30, provided that when B25 is Tyr then B30 is different from Ala.

Thus, the human insulin analogs of the invention are advantageous in the treatment of Diabetes, as the increased biological activity resulting from the replacements in the B25-position means a more rapid absorption from the blood and moreover may neutralize the decrease of biological activity which may otherwise be the result of other substitutions in the human insulin molecule.

A particular embodiment of the invention is represented by human insulin analogs containing $[His^{B25}]$ or $[Tyr^{B25}]$ and at least one substitute amino acid residue selected from the group consisting of $[Gln^{A4}]$, $[His^{A8}]$, $[Gln^{A17}]$, $[Asp^{A21}]$, $[Asp^{B9}]$, $[Asp^{B10}]$, $[Ile^{B12}]$, $[Gln^{B13}]$, $[Arg^{B13}]$, $[Gln^{B21}]$, $[Pro^{B21}]$, $[Glu^{B26}]$, $[Arg^{B27}]$, $[Asp^{B28}]$, $[Ala^{B30}]$, and $[Ser^{B30}]$, provided that when B25 is Tyr then B30 is different from Ala.

Another particular embodiment of the invention is represented by human insulin analogs containing $[His^{B25}]$ or $[Tyr^{B25}]$ and at least two substitute amino acid residues selected from the group consisting of $[Gln^{A4}]$, $[His^{A8}]$, $[Gln^{A17}]$, $[Gln^{B13}]$, $[Arg^{B13}]$, $[Gln^{B21}]$, $[Ile^{B21}]$, $[Arg^{B27}]$, $[Ala^{B30}]$, and $[Ser^{B30}]$, provided that when B25 is Tyr then B+is different from Ala.

Yet another particular embodiment of the invention is represented by human insulin analogs containing $[His^{B25}]$ or $[Tyr^{B25}]$ and at least two substitute amino acid residues selected from the group consisting of [His$^{A8}$], [Asp$^{A21}$], [Asp$^{B9}$], [Asp$^{B10}$], [Ile$^{B12}$], [Glu$^{B26}$], [Asp$^{B28}$], [Ala$^{B30}$], and [Ser$^{B30}$], provided that when B25 is Tyr then B30 is different from Ala.

Preferred human insulin analogs of the invention are [Tyr$^{B25}$]-human insulin
[Tyr$^{B25}$, Asp$^{B28}$]-human insulin
[His$^{B25}$]-human insulin
[His$^{B25}$, Asp$^{B28}$]-des[Thr$^{B30}$]-human insulin
[Tyr$^{B25}$]-human insulin-$B30$-amide
[His$^{B25}$]-human insulin-$B30$-amide.

The described insulin derivatives can be produced biosynthetically in yeast expressing a DNA-sequence encoding a given insulin precursor. After the biosynthesis this precursor can be converted into the insulin derivative by an enzymatically catalyzed reaction. To achieve secretion to the growth medium, the DNA-sequence encoding the insulin precursor can be fused to another DNA-sequence encoding a signal peptide functional in yeast. Secretion can be achieved by insertion in the expression plasmid of the Saccharomyces cerevisiae MFα1-leader sequence (Kurjan & Herskowitz, Cell 30, 933–943 (1982). A preferred construction uses the DNA-sequence encoding the entire MFα1-leader sequence including the dibasic site LysArg but excluding the peptide sequence GluAlaGluAla which is the substrate for the yeast protease DPAP (dipeptidyl aminopeptidase). In that way, an efficient secretion of insulin precursors with the correct N-terminal is achieved.

DNA-sequences encoding modified insulin precursors were constructed with basis in the expression cassette which is contained in the BamHI restriction fragment from the expression plasmid pYGABA as shown in FIG. 1, has a length of 1103 basepairs and contains essentially the following (listed in succession starting from the 5'-end): The GAPDH promoter (Travis et al., J. Biol. Chem., 260, 4384–4389 (1985) followed by the coding region consisting of: The 83 N-terminal amino acids of the MFα1-leader sequence encoded by the wild-type yeast DNA sequence as described by Kurjan & Herskowitz (reference given above) followed by the two codons AAA and AGA encoding Lys and Arg and again followed by the coding region for the insulin precursor single chain des[Thr$^{B30}$]-human insulin (SCI), which is a synthetically constructed gene using preferred yeast codons. After two stop-codons, a SalI restriction site is positioned, and the rest of the sequence constitutes the MFα1-sequence containing the terminator region. The sequence is constructed using entirely standard techniques.

The method employed was "oligonucleotide site directed mutagenesis", which is described by Zoller & Smith, DNA, Vol. 3, No. 6, 479–488 (1984). The method is briefly described in the following, and is described thoroughly in Example 1. Isolated from the expression plasmid the insulin precursor sequence is inserted into a single-stranded, circular M13 bacteriophage vector. To the single-stranded genom, a chemically synthesized complementary DNA-strand is annealed. The DNA-strand contains the desired sequence surrounded by sequences completely homologous to insulin sequences on the circular DNA. In vitro, the primer is then extended in the entire length of the circular genom biochemically using Klenow polymerase. This strand will give rise to single-stranded phages, which when grown in E.coli give the possibility to isolate double-stranded DNA with the desired sequence. From this double-stranded DNA, a restriction fragment can be isolated and reinserted into the expression vector.

Human insulin analogs of the invention in which possible substitutions are only present within the last amino acid residues nearest to the C-terminal of the B-chain may moreover in a manner known per se be prepared semisynthetically from e.g. porcine insulin as described in K. Inouye et al.: JACS 101 (3), p. 751–52 (1979), whereby the porcine insulin is first split with trypsin to des-(B23–30)-human insulin, whereupon the latter, also enzymatically, is coupled with a synthetic peptide having the desired amino acid sequence.

The invention also relates to insulin preparations which besides the usual adjuvants, excipients and/or carriers comprise at least one human insulin analog in which the amino acid residue in position B25 is His or Tyr, the amino acid residue in one or more of the positions A4, A8, A17, A21, B9, B10, B12, B13, B21, B26, B27, B28, and B30 is optionally substituted, and the amino acid residue in the B30-position is optionally missing or blocked at the C-terminal in the form of ester or amide. The insulin preparations of the invention may be prepared according to conventional methods for preparing insulin preparations.

MODES FOR CARRYING OUT THE INVENTION

The invention is further illustrated by the following Examples.

EXAMPLE I

Construction of an expression plasmid, which can be used to express [Tyr$^{B25}$]-SCI.

The expression cassette, which is contained in the expression plasmid pYGABA (shown in FIG. 1) on a BamHI restriction fragment, was isolated: The expression plasmid was incubated with the restriction endonuclease BamHI. The conditions were: 20 μg of plasmid, 50 units of BamHI, 100 mM NaCl, 50 mM Tris-HCl, pH 7.5, 10 mM MgCl$_2$, and 1 mM DTT in a volume of 100 μliters. The temperature was 37° C. and the reaction time 2 hours. The two DNA-fragments were separated on a 1% agarose gel, and the desired fragment was isolated.

Ligation to the M13 vector M13mp18:

The isolated restriction fragment was ligated to the bacteriophage vector M13mp18 also cut with the restriction endonuclease BamHI in the following reaction mixture: Fragment 0.2 μg, vector 0.02 μg, 50 mM Tris-HCl, pH 7.4, 10 mM MgCl$_2$, 10 mM DTT and 1 mM ATP in a volume of 20 μliters. 5 μliters of this mixture were transformed into the E. coli strain JM101. The presence of fragment in the vector and the orientation of the fragment was determined by restriction enzyme mapping on double-stranded M13-DNA isolated from the transformants.

Transformation of JM101:

The reaction mixture above was transformed in different dilutions into CaCl$_2$-treated E.coli JM101 cells using standard techniques and plated in 2×YT topagar on 2×YT agar plates. (2×YT=tryptone 16 g/liter, yeast extract 10 g/liter, NaCl 5 g/liter. 2×YT topagar=2×YT with 0.4% agarose added and autoclaved. 2×YT agar plates=2×YT with 2% agar added and autoclaved). The plates were incubated at 37° C. overnight.

Identification of positive clones:

The method used was plaque-lift hybridisation which is described in the following: a nitrocellulose-filter was placed on a plate with a suitable plaque-density, so that the filter was wetted. The filter was then bathed in the following solutions: 1.5M NaCl, 0.5 M NaOH for 30 sec., 1.5M NaCl, 0.5M Tris-HCl, pH 8.0 for 1 min., 2×SSC (0.3M NaCl, 0.03 M sodium citrate) till later use. The filter was dried on 3 MM filter paper and baked for 2 hours at 80° C. in a vacuum oven.

The mutagenisation primer with the sequence 5'-TGGAGTGTAGTA-GAAACCTCT-3' was labelled radioactively in the 5' end in a 30 μliters volume containing 70 mM Tris-HCl, pH 7.5, 10 mM MgCl$_2$, 5 mM DTT, 10 pmol oligonucleotide 20 pmol γ-$^{32}$P-ATP and 3.5 units of T4 polynucleotide kinase. The mixture was incubated at 37° C. for 30 min. and then for 5 min. at 100° C.

The dried filter was pre-hybridised for 2 hours at 65° C. in 6×SSC, 0.2% bovine-serum albumin, 0.2% Ficoll, 0.2% polyvinylpyrrolidon, 0.2% sodium-dodecyl-sulphate (SDS) and 50 μg/ml salmon-sperm DNA. Then, the reaction mixture containing the labelled probe was added to 15 ml of fresh pre-hybridisation mix, and the filter was bathed herein overnight at 31° C. with gentle shaking. After hybridisation, the filter was washed 3 times for each 15 min. in 2×SSC+0.1% SDS and autoradiographed. After wash in the same solution, but now at 61° C., and another autoradiography, plaques containing DNA-sequences complementary to the mutagenisation primer were identified.

Re-screening of positive clones:

Because the identified clone is a result of a heteroduplex, the plaque was plated again. The hybridisation and identification were repeated.

Purification of double-stranded M13-phage DNA:

A re-screened clone was used for infection of the *E. coli* strain JM101. A culture containing approximately 10$^8$ phages and 5 colonies of JM101 was grown for 5 hours in a 5 ml 2×YT medium at 37° C. Then, double-stranded, circular DNA was purified from the pellet according to a method described by Birnboim & Doly, Nucleic Acids Res., 2, 1513 (1979).

Isolation of single-stranded (ss) DNA (template):

From the transformant described above ss-DNA was isolated according to a method described by Messing in Gene, 19, 269-276 (1982).

5'-phosphorylation of the mutagenisation primer:

The mutagenisation primer with the sequence 5'-TGGAGTGTAGTA-GAAACCTCT-3' was phosphorylated in the 5'-end in a 30 μliters reaction mixture containing 70 mM Tris-HCl, pH 7.0, 10 mM MgCl$_2$, 5 mM DTT, 1 mM ATP, 100 pmol oligonucleotide and 3.6 units of T4 polynucleotide kinase. The reaction was carried out for 30 min. at 37° C. Then, the enzyme was inactivated by incubating the mixture for 10 min. at 65° C.

Annealing of template and mutagenisation primer:

Annealing of template and primer was carried out in a 10 μliters volume containing 0.5 pmol template, 4 pmol primer, 20 mM Tris-HCl, pH 7.5, 10 mM MgCl$_2$, 50 mM NaCl and 1 mM DTT by heating for 10 min. at 65° C. and cooling afterwards to 0° C.

Extension/ligation reaction:

To the reaction mixture above, 10 μliters of the following mixture were added: 0.3 mM dATP, 0.3 mM dCTP, 0.3 mM dGTP, 0.3 mM TTP, 1 mM ATP, 20 mM Tris-HCl, pH 7.5, 10 mM MgCl$_2$, 10 mM DTT, 3 units of T4 DNA ligase and 2.5 units of Klenow polymerase. Then, the reaction was carried out for 16 hours at 16° C.

Isolation of a restriction fragment containing modified insulin precursor:

The DNA-preparation (appr. 5 μg) isolated above was digested with 10 units of the restriction endonuclease BamHI in 60 μliters of 100 mM NaCl, 50 mM Tris-HCl, pH 7.5, 10 mM MgCl$_2$, and 1 mM DTT for 2 hours at 37° C. The DNA-products were separated on an agarose-gel, and the fragment was purified from the gel.

Figure 2:
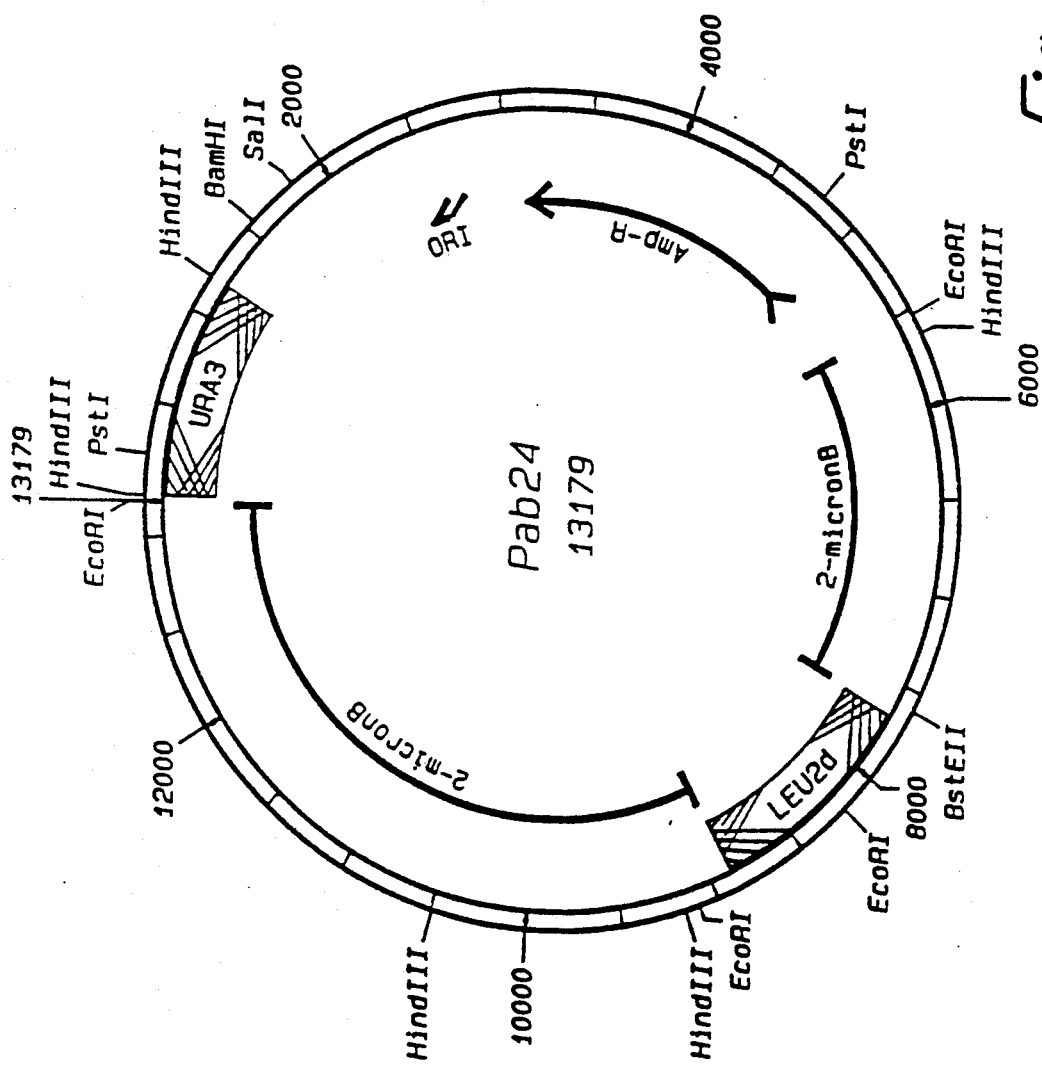

Ligation to the yeast vector pAB24 (FIG. 2):

The isolated restriction fragment was ligated to the yeast vector pAB24 digested with the restriction endonuclease BamHI in the following reaction mixture: Fragment 0.2 μg, vector 0.02 μg, 50 mM Tris-HCl, pH 7.4, 10 mM MgCl$_2$, 10 mM DTT, 1 mM ATP in a total volume of 20 μliters. 5 μliters of this reaction mix was used for transformation of the *E. coli* strain MC1061, in which the modified expression plasmid was identified and propagated. The plasmid was identical to pYGABA, except for the changed codon.

Transformation of yeast:

Transformation of the expression plasmid into the yeast strain *Saccharomyces cerevisiae* JC482ΔpepΔLeu2-ciro$^o$ (α, his4, ura3, leu2, cir$^o$) was carried out as described by Ito et al., J. Bact., Vol. 153, No. 1, 163-168 (1983). The transformed cells were plated on SC-ura medium (0.7% Yeast Nitrogen Base, 2.0% glucose, 0.5% casamino acids, 2.0% agar) for selection for plasmid-containing cells.

EXAMPLE II

Construction of an expression plasmid, which can be used for production of [His$^{B25}$, Asp$^{B28}$]-SCI.

The procedure used was essentially the same as described in Example I, except that the mutagenisation primer had the sequence 5'ACAATACCCTTGT-CAGTGTAGTGGAAACCTCTTT3', that the hybridisation temperature was 42° C., and that the washing temperature after the hybridisation was 63° C. The modified plasmid had a sequence identical to pYGABA, except for the modified codons.

EXAMPLE III

Expression of precursor and isolation from the culture medium.

Yeast, transformed as described in Example I or II, was propagated on Petri-plates containing minimal-medium without uracil for 48 hours at 30° C. 100 ml shake bottles containing minimal-medium without uracil+5 g/liter casamino acids+10 g/liter succinic acid+30 g/liter glucose at pH 5.0 was inoculated with a single colony from the Petri-plate. The bottles were then shaken at 30° C. in incubator for 72 hours.

After centrifugation 1 liter of pooled supernatant was sterilized by filtration and adjusted to pH 4-4.5 and a conductivity<10 mS by addition of 5M HCl and water. With a flow of 120 ml/hour the supernatant was then applied to a 1.6×6 cm column of S-Sepharose® FF previously equilibrated with 50 mM acetic acid, 50% (by volume) ethanol adjusted to pH 4.0 with NaOH. The column was washed with 60 ml buffer and the precursor was then eluted by a linear gradient of NaCl from 0 to 0.35 M in 360 ml buffer with a flow of 10 ml/hour. The eluate was divided in fractions of 4 ml and detected for UV-absorbance. Fractions containing precursor were identified by RP-HPLC analysis and were pooled. After desalting on a column of Sephadex® G25 in 1 M acetic acid the precursor was isolated by lyophilization.

EXAMPLE IV

Preparation of [Tyr$^{B25}$]-des[Thr$^{B30}$]-human insulin from precursor.

450 mg of [Tyr$^{B25}$]-SCI, prepared by the methods described in Examples I and III, were dissolved in 45 ml of 50 mM tris(hydroxymethyl)aminomethane, 20% (by volume) ethanol adjusted to pH 7.7 with HCl and 45 ml (settled volume) of Sepharose ® containing 36 mg of immobilized trypsin in the same buffer were added. The suspension was left for 3 hours at 20° C. with gentle agitation and was then filtered. The gel was washed with 40 ml of buffer, and the pooled filtrates were applied to a 2.6×7.5 cm column of Q-Sepharose ® FF previously equilibrated with 50 mM tris(hydroxymethyl)aminomethane, 50% (by volume) ethanol, adjusted to pH 8.0 with HCl. The column was then eluted with a linear gradient of NaCl from 0 to 0.15M in the same buffer over 6 hours with a flow of 225 ml/hour. The eluate was detected for UV-absorbance and fractions containing the main protein peak were pooled.

After dilution with the same volume of water the pool was applied to a 2.6×25 cm column of Lichroprep ® RP-18 (25-40 µm) previously equilibrated with 10 mM H$_3$PO$_4$, 0.1M NaCl, 30% (by volume) ethanol. With a flow of 16 ml/hour the column was then eluted with a linear gradient of ethanol from 30% to 40% (by volume) over 20 hours. The eluate was detected for UV-absorbance and fractions containing the main protein peak were pooled. After desalting on a column of Sephadex ® G25 in 1M acetic acid 105 mg of [Tyr$^{B25}$]-des[Thr$^{B30}$]-human insulin were isolated by lyophilization.

The protein was redissolved in a mixture containing 200 mg of threonine methyl ester, 1.0 ml of ethanol and 0.4 ml of water. The pH value was adjusted to 6.3 with acetic acid, and 2 ml (settled volume) of Sepharose ® containing 1.6 mg of immobilized trypsin were added. After standing for 2 hours at 20° C. with gentle agitation, the gel was removed by filtration, and the protein was precipitated by addition of 10 volumes of 2-propanol. The air-dried precipitate was redissolved in 20 mM tris(hydroxymethyl)aminomethane/HCl, 60% (by volume) ethanol, pH 8.25, and applied to a 1.6×20 cm Q-Sepharose ® FF column, previously equilibrated with the said buffer, and eluted with a linear NaCl-gradient in the same buffer increasing from 0 to 0.1M over 15 hours at a flow rate of 50 ml/hour. The ethanol was removed in vacuo from the pooled fractions containing [Tyr$^{B25}$] human insulin-(B30-methyl ester), and the protein was precipitated by adjusting the pH value to 6.1. After centrifugation and lyophilization the methyl ester was hydrolyzed for 10 min. in cold 0.1M NaOH at a protein concentration of 10 mg/ml. The reaction was stopped by adjusting the pH value to 8.5, and 2 volumes of 20 mM tris(hydroxymethyl)aminomethane/HCl, pH 8.5, were added. The solution was then applied to a 1.6×20 cm Q-Sepharose ® FF column and eluted as described above. The protein was precipitated at a pH value of 5.5 after removal of the ethanol in vacuo. 40 mg of [Tyr$^{B25}$]-human insulin were obtained after lyophilization.

The identity of the product was confirmed by amino acid analysis and by sequential Edman degradation of the separated vinylpyridylated A- and B-chains.

EXAMPLE V

Preparation of [His$^{B25}$, Asp$^{B28}$]-des[Thr$^{B30}$]-human insulin from precursor.

100 mg of [His$^{B25}$, Asp$^{B28}$]-SCI, prepared by the methods described in Examples II and III, were dissolved in 10 ml of 50 mM tris(hydroxymethyl)aminomethane, 20% (by volume) ethanol, adjusted to pH 7.7 with HCl and 10 ml (settled volume) of Sepharose ®, containing 8 mg of immobilized trypsin, in the same buffer were added. The suspension was left for 3 hours at 20° C. with gentle agitation and was then filtered. The gel was washed with 10 ml of buffer, and the pooled filtrates were applied to a 1.6×7.5 cm column of Q-Sepharose ® FF previously equilibrated with 50 mM tris(hydroxymethyl)aminomethane, 50% (by volume) ethanol, adjusted to pH 8.0 with HCl. The column was then eluted with a linear gradient of NaCl from 0 to 0.15M in the same buffer over 6 hours with a flow of 90 ml/hour. The eluate was detected for UV-absorbance, and fractions containing the main protein peak were pooled.

After dilution with the same volume of water the pool was applied to a 1.6×25 cm column of Lichroprep ® RP-18 (25-40 um) previously equilibrated with 10 mM H$_3$PO$_4$, 0.1M NaCl, 30% (by volume) ethanol. With a flow of 6.5 ml/hour the column was then eluted with a linear gradient of ethanol from 30% to 40% (by volume) over 20 hours. The eluate was detected for UV-absorbance, and fractions containing the main protein peak were pooled. After desalting on a column of Sephadex ® G25 in 1M acetic acid 39 mg of [His$^{B25}$, Asp$^{B28}$]-des[Thr$^{B30}$]-human insulin were isolated by lyophilization.

The identity of the product was confirmed by amino acid analysis and by sequential Edman degradation of the separated vinylpyridylated A- and B-chains.

EXAMPLE VI

Preparation of des-(B23-B30)-human insulin.

1 g of Na-crystallized porcine insulin (protein weight) was dissolved in 40 ml of water, and a solution of 50 mg of porcine trypsin in 10 ml of freshly prepared 0.25M ammonium hydrogencarbonate solution in which pH has been adjusted to 9.0 with ammonia water was added. Then, the solution was left in a refrigerator at 4° C. After 48 hours a HPLC analysis showed a degree of reaction of 65%. Thereafter the solution was gel-filtered at 4° C. on a 5×90 cm column of Sephadex ® G50 Superfine in 0.05M ammonium hydrogencarbonate at a flow of 90 ml/hour. Fractions containing the main protein peak were pooled and lyophilized.

Yield: 520 mg of des-(B23-30)-human insulin of a purity of 97.5%, measured by HPLC analysis.

EXAMPLE VII

Preparation of peptides.

Peptides were prepared by means of a peptide synthesis machine from Applied Biosystems, whereby the construction was made on a PAM resin by means of protected symmetrical amino acid anhydrides. The capacity was about 0.1 mmole of peptide. Finally, the peptide was split from the resin by reaction with anhydrous hydrogen fluoride at 0° C., whereby the remaining protection groups were simultaneously removed.

EXAMPLE VIII

Preparation of [His$^{B25}$]-human insulin.

200 mg of des-(B23-30)-human insulin and 400 mg of Gly-Phe-His-Tyr-Thr-Pro-Lys-Thr were dissolved in a mixture of 2.40 ml of dimethyl formamide and 1.20 ml of water, the pH of the mixture being adjusted to 6.5 with triethyl amine.

Then, a solution of 10 mg of porcine trypsin in 0.20 ml of water was added, and the reaction mixture was left at 20° C. After 4 hours a HPLC analysis showed a reaction of 60%, and the reaction was stopped by precipitation with 25 ml of 2-propanol. The precipitate which was isolated by centrifugation was redissolved in 10 ml of 1M acetic acid and applied at 20° C. to a 2.6×20 cm column of Lichroprep ® RP-18 (25-40 μm), equilibrated in a buffer consisting of 0.5 mM hydrogenchloride, 0.1M sodium chloride in 30% (by volume) ethanol. Then the column was eluted with the same buffer at a flow of 20 ml/hour, the content of ethanol however being linearly increased to 50% over 24 hours. The fractions containing the main protein peak were pooled, whereupon the protein was precipitated by dilution with the same volume of water and adjustment of pH to 5.5 with sodium hydroxide solution. After standing at 4° C. for 1 hour the suspension was centrifuged, and the precipitate was freeze-dried. Hereby 90 mg of [His$^{B25}$]-human insulin were obtained, identified by total amino acid analysis and by sequential Edman degradation of the separated vinylpyridylated A- and B-chains.

EXAMPLE IX

Preparation of [Tyr$^{B25}$, Asp$^{B28}$]-human insulin.

150 mg of des-(B23-30)-human insulin and 350 mg of Gly-Phe-Tyr-Tyr-Thr-Asp-Lys-Thr were dissolved in a mixture of 2.0 ml of dimethyl formamide and 1.0 ml of water, the pH being adjusted to 6.5 with triethyl amine. Now a solution of 8 mg of porcine trypsin in 0.20 ml of 1 mM calcium acetate solution was added, and the reaction mixture was left at 15° C. After 3 hours a HPLC analysis showed a reaction of 50%, and the reaction was stopped by adding 25 ml of 2-propanol.

After centrifugation the precipitate was redissolved in 10 ml of 1M acetic acid and applied at 20° C. to a 2.6×20 cm column of Lichroprep ® RP-18 (25-40 μm), equilibrated in a buffer consisting of 0.5 mM hydrogenchloride, 0.1M sodium chloride in 30% (by volume) ethanol. Then, the column was eluted with the same buffer at a flow of 20 ml/hour, the content of ethanol however being linearly increased to 50% over 24 hours. The fractions containing the main protein peak were pooled, whereupon the protein was precipitated by dilution with the same volume of water and adjustment of pH to 5.0 with sodium hydroxide solution. After standing overnight at 4° C. the precipitate was isolated by centrifugation and freeze-dried.

Yield: 60 mg of [Tyr$^{B25}$, Asp$^{B28}$]-human insulin, identified by total amino acid analysis and by sequential Edman degradation of the separated vinylpyridylated A- and B-chains.

EXAMPLE X

Evaluation of biological activity.

The biological activity in vitro was determined by measuring the binding affinity to the insulin receptors of isolated rat adipocytes and hepatocytes essentially as described in J. Gliemann, S. Gammeltoft: Diabetologia 10, 105-113 (1974).

The insulin analogs were compared to semisynthetic human insulin, the potency of which was set to 100%, and the results are shown in the Table below:

|  | Adipocytes | Hepatocytes |
| --- | --- | --- |
| [Tyr$^{B25}$]-human insulin | 356 % | 222% |
| [Tyr$^{B25}$, Asp$^{B28}$]-human insulin | 201% | 138% |
| [His$^{B25}$]-human insulin | 150% | 142% |
| [His$^{B25}$, Asp$^{B28}$]-des[Thr$^{B30}$]-human insulin | 130% | 135% |

We claim:

1. Human insulin analogs exhibiting high biological activity, characterized in that the amino acid residue in position B25 is His or Tyr, that the amino acid residue in one or more of the positions A4, A8, A17, A21, B9, B10, B12, B13, B21, B26, B27, B28, and B30 is optionally replaced by another amino acid residue, and that the amino acid residue in the B30-position is optionally missing or blocked at the C-terminal in the form of ester or amide, provided that when B25 is Tyr then B30 is different from Ala.

2. Human insulin analogs according to claim 1, characterized by containing [His$^{B25}$] or [Tyr$^{B25}$] and at least one substitute amino acid residue selected from the group consisting of [Gln$^{A4}$], [His$^{A8}$], [Gln$^{A17}$], [Asp$^{A21}$], [Asp$^{B9}$], [Asp$^{B10}$], [Ile$^{B12}$], [Gln$^{B13}$], [Arg$^{B13}$], [Gln$^{B21}$], [Pro$^{B21}$], [Glu$^{B26}$], [Arg$^{B27}$], [Asp$^{B28}$], [Ala$^{B30}$], and [Ser$^{B30}$], provided that when B25 is Tyr then B30 is different from Ala.

3. Human insulin analogs according to claim 1, characterized by containing [$^{B25}$] or [Tyr$^{B25}$] and at least two substitute amino acid residues selected from the group consisting of [Gln$^{A4}$], [His$^{A8}$], [Gln$^{A17}$], [Gln$^{B13}$], [Arg$^{B13}$], [Gln$^{B21}$], [Ile$^{B21}$], [Arg$^{B27}$], [Ala$^{B30}$], and [Ser$^{B30}$], provided that when B25 is Tyr then B30 is different from Ala.

4. Human insulin analogs according to claim 1, characterized by containing [His$^{B25}$] or [Tyr$^{B25}$] and at least two substitute amino acid residues selected from the group consisting of [His$^{A8}$], [Asp$^{A21}$], [Asp$^{B9}$], [Asp$^{B10}$], [Ile$^{B12}$], [Glu$^{B26}$], [Asp$^{B28}$], [Ala$^{B30}$], and [Ser$^{B30}$], provided that when B25 is Tyr then B30 is different from Ala.

5. Human insulin analog according to claim 1, characterized by being [Tyr$^{B25}$]-human insulin.

6. Human insulin analog according to claim 1, characterized by being [Tyr$^{B25}$, Asp$^{B28}$]-human insulin.

7. Human insulin analog according to claim 1, characterized by being [His$^{B25}$]-human insulin.

8. Human insulin analog according to claim 1, characterized by being [His$^{B25}$, Asp$^{B28}$]-des-[Thr$^{B30}$]-human insulin.

9. Human insulin analog according to claim 1, characterized by being [Tyr$^{B25}$]-human insulin-B30-amide.

10. Human insulin analog according to claim 1, characterized by being [His$^{B25}$]-human insulin-B30-amide.

11. Insulin preparation, characterized by containing at least one human insulin analog in which the amino acid residue in position B25 is His or Tyr, the amino acid residue in one or more of the positions A4, A8, A17, A21, B9, B10, B12, B13, B21, B26, B27, B28, and B30 is optionally replaced by another amino acid residue, and the amino acid residue in the B30-position is optionally missing or blocked at the C-terminal in the form of ester or amide, provided that when B25 is Tyr then B30 is different from Ala.

12. Insulin preparation according to claim 11, characterized by containing at least one human insulin analog comprising [His$^{B25}$] or [Tyr$^{B25}$] and at least one substitute amino acid residue selected from the group consisting of [Gln$^{A4}$], [His$^{A8}$], [Gln$^{A17}$], [Asp$^{A21}$], [Asp$^{B9}$], [Asp$^{B10}$], [Ile$^{B12}$], [Gln$^{B13}$], [Arg$^{B13}$], [Gln$^{B21}$], [Ile$^{B21}$], [Glu$^{B26}$], [Arg$^{B27}$], Asp$^{B28}$], [Ala$^{B30}$], and [Ser$^{B30}$].

13. Insulin preparation according to claim 11, characterized by containing at least one human insulin analog comprising [His$^{B25}$] or [Tyr$^{B25}$] and at least two substitute amino acid residues selected from the group consisting of [Gln$^{A4}$], [His$^{A8}$], [Gln$^{A17}$], [Gln$^{B13}$], [Arg$^{B13}$], [Gln$^{B21}$], [Ile$^{B21}$], [Arg$^{B27}$], [Ala$^{B30}$] and [Ser$^{B30}$].

14. Insulin preparation according to claim 11, characterized by containing at least one human insulin analog comprising [His$^{B25}$] or [Tyr$^{B25}$] and at least two substitute amino acid residues selected from the group consisting of [His$^{A8}$], [Asp$^{A21}$], [Asp$^{B9}$], [Asp$^{B10}$], [Ile$^{B12}$], [Glu$^{B26}$], [Asp$^{B28}$], [Ala$^{B30}$], and [Ser$^{B30}$].

15. Insulin preparation according to claim 11, characterized by containing [Tyr$^{B25}$]-human insulin.

16. Insulin preparation according to claim 11, characterized by containing [Tyr$^{B25}$, Asp$^{B28}$]-human insulin.

17. Insulin preparation according to claim 11, characterized by containing [His$^{B25}$]-human insulin.

18. Insulin preparation according to claim 11, characterized by containing [His$^{B25}$, Asp$^{B28}$]-des-[Thr$^{B30}$]-human insulin.

19. Insulin preparation according to claim 11, characterized by containing [Tyr$^{B25}$]-human insulin-B30-amide.

20. Insulin preparation according to claim 11, characterized by containing [His$^{B25}$]-human insulin-B30-amide.

* * * * *

UNITED STATES PATENT AND TRADEMARK OFFICE
CERTIFICATE OF CORRECTION

PATENT NO. : 5,149,777

DATED : September 22, 1992

INVENTOR(S) : Finn B. Hansen and Per Balschmidt

It is certified that error appears in the above-identified patent and that said Letters Patent is hereby corrected as shown below:

Column 2, line 33, change "IIe" to --Ile--;

Column 2, line 64, change "B+" to --B30--;

Column 3, line 10, change "B30" to --B30--;

Column 3, line 11, change "B30" to --B30--;

Column 6, line 25, change "ciro°" to --cir°--;

Column 10, line 33, change "[$B25$]" to --[$His^{B25}$]--; and

Column 11, line 7, change "$Asp^{B28}$]" to --[$Asp^{B28}$].

Signed and Sealed this

Ninth Day of May, 1995

*Attest:*

BRUCE LEHMAN

*Attesting Officer*     Commissioner of Patents and Trademarks